United States Patent
Ohkuma et al.

(10) Patent No.: US 7,022,311 B1
(45) Date of Patent: Apr. 4, 2006

(54) POWDERY INHALATIONAL PREPARATIONS AND PROCESS FOR PRODUCING THE SAME

(75) Inventors: Moriyuki Ohkuma, Shizuoka (JP);
Keiko Matsumoto, Shizuoka (JP);
Otomo Okuda, Shizuoka (JP);
Yasutomi Kato, Shizuoka (JP);
Yoshiaki Kawashima, Gifu (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/110,340

(22) PCT Filed: Oct. 12, 2000

(86) PCT No.: PCT/JP00/07089

§ 371 (c)(1),
(2), (4) Date: Aug. 7, 2002

(87) PCT Pub. No.: WO01/26630

PCT Pub. Date: Apr. 19, 2001

(30) Foreign Application Priority Data

Oct. 12, 1999 (JP) ............................ 11/289031
Jun. 19, 2000 (JP) ............................ 2000/183469

(51) Int. Cl.
*A61K 9/12* (2006.01)
*A61K 9/14* (2006.01)

(52) U.S. Cl. ................ 424/45; 424/46; 424/489; 424/499; 514/951

(58) Field of Classification Search ................ 424/45, 424/46, 489, 689, 499, 434; 514/781, 958, 514/218, 2, 3, 951; 128/203.12

See application file for complete search history.

(56) References Cited

U.S. PATENT DOCUMENTS

| | | | |
|---|---|---|---|
| 5,607,662 A | 3/1997 | Baskeyfield et al. | |
| 5,908,639 A | 6/1999 | Simpkin et al. | |
| 5,952,008 A * | 9/1999 | Backstrom et al. | 424/499 |
| 5,972,388 A | 10/1999 | Sakon et al. | |
| 6,153,224 A * | 11/2000 | Staniforth | 424/490 |
| 6,284,282 B1 * | 9/2001 | Maa et al. | 424/499 |
| 6,284,287 B1 | 9/2001 | Sarlikiotis et al. | |
| 6,589,554 B1 * | 7/2003 | Mizumoto et al. | 424/465 |
| 6,645,466 B1 * | 11/2003 | Keller et al. | 424/43 |

FOREIGN PATENT DOCUMENTS

| | | |
|---|---|---|
| EP | 0 611 567 A1 | 8/1994 |
| GB | 1381872 | 1/1975 |
| WO | WO 93/25198 | 6/1993 |
| WO | WO 93/17663 | 9/1993 |
| WO | WO 94/04133 | 3/1994 |
| WO | WO 96/02231 | 2/1996 |

* cited by examiner

*Primary Examiner*—Sreeni Padmanabhan
*Assistant Examiner*—Mina Haghighatian
(74) *Attorney, Agent, or Firm*—Fitch, Even, Tabin & Flannery

(57) ABSTRACT

The present invention is aimed at providing a dry powder inhalation with minimal adhesive-agglomerative property during storage and with a good inhalation behavior for a pharmaceutically active ingredient, and is a dry powder inhalation wherein at least an active ingredient is adhered to the surface of a carrier particle comprised of erythritol and/or trehalose. It is also a dry powder inhalation wherein at least S-36496 and/or Pralmorelin dihydrochloride is adhered to the surface of the carrier particle. It is further a dry powder inhalation wherein at least an active ingredient and a surface modifier are adhered to the surface of the carrier particle. It is also a preparation method of these. Said dry powder inhalation may be applied to the capsules for use in an inhaler device. In addition to the achievement of above objectives, the present invention provides a dry powder inhalation with improved taste in inhalation or with reduced discomfort in the oral cavity and the throat, and a preparation method for enabling an easy preparation thereof without complicated processes.

19 Claims, No Drawings

POWDERY INHALATIONAL PREPARATIONS AND PROCESS FOR PRODUCING THE SAME

CROSS-REFERENCED APPLICATIONS

This application is a National phase of International Application PCT/JP00/07089, filed Oct. 12, 2000, which designated the U.S. and that International Application was not published under PCT Article 21(2) in English.

TECHNICAL FIELD

The present invention relates to a capsulated dry powder inhalation. It further relates to a dry powder inhalation wherein at least a micronized pharmaceutically active ingredient is adhered to the surface of a carrier particle; a method for preparation thereof; and a capsulated formulation for use in an inhaler device, in which a capsule is filled with an inhalant medication.

BACKGROUND TECHNOLOGY

Inhalant is a dosage form used for the oral or nasal inhalation of a drug formulation for administering a pharmaceutically active ingredient mainly to the lower respiratory tracts such as the trachea, bronchi, bronchiole, pulmonary alveoli, and the like.

Inhalant has been used as a topically administered formulation for thoracic diseases such as asthma, bronchitis, emphysema, and the like, and further it is recently attracting attention as means to deliver a physiologically active peptide, protein, and the like through the pulmonary alveoli to the systemic bloodstream. In general, inhalants directly deliver the active ingredient to the lungs, are therefore instantaneously effective, and require only a smaller dose of an active ingredient than an oral dosage form. As a result, this provides considerable advantage such as a reduced side effect.

Inhalants may be classified into liquid inhalants for inhaling a liquid, aerosol using a spray aerosol generator, and powder inhalants for inhaling a powdery drug. However, because of the environmental problems associated with CFC propellants, recent trends have led to powder inhalants being preferentially developed.

The most preferred form for the powder preparation used in powder inhalants (hereafter, dry powder inhalation) is a dosage form in which a micronized active ingredient is adhered to the surface of carrier particles.

It is important for a dry powder inhalation to be inhalable, in particular, it is required that the carrier and drug particles must separate well, that the micronized particles do not remain adhered to the powder dispersion device used during inhalation, and that the drug particles be uniformly dispersed in the gas phase.

Processes are presently known for the pulverization of active ingredients, such as a freeze dry method (Japanese Patent Application Laid-Open No. H06-100464), a solvent process using a spray dry method (Japanese Patent Application Laid-Open No. H11-79985), and a crystallization method (Japanese Patent Laid-Open No. H8-291073), but the use of solvent creates environmental problems and the use of solvent is not possible if the active ingredient is unstable in the solvent, prompting the need for a solvent-free preparation method.

When a dry powder inhalation is administered from a suitable inhaler device into the respiratory tract, the carrier particles would deposit in the oral cavity, throat, or larynx, but the active ingredient particulates alone would reach, and deposit on, the lower respiratiory tracts such as the trachea, bronchi, and the like. However, if a bitter tasting active ingredient is used, the bitterness felt in the oral cavity or in the throat will create much discomfort. In particular, since many pediatric and elderly patients use the device, the dry powder inhalation would not necessarily be a liked dosage form, which calls for an improvement in the taste. It is conceivable to mask the bitterness of the active ingredient to reduce the discomfort, but masking is extremely difficult with a micronized active ingredient.

Powder inhaler medication, in which the active ingredients and carrier particles are fine powders, must in general contain an antistatic agent to prevent the each particles from adhesion and agglomeration. Japanese Patent Kohyo Publication No. H8-500109 (a Japanese translation of a PCT international application) describes that fatty acid esters are effective antistatic agents, but their being liquid requires a step for drying the carrier particles first before being mixed with the active ingredient, which makes it difficult to apply to a dry type preparation method. On the other hand, Japanese Patent Kohyo Publication No. H10-502647 (a Japanese translation of a PCT application) teaches a preparation method of a dry powder inhalation without using an antistatic agent by adjusting the particle size of the carrier particles to render them unadherable, but the particle size required is as large as 200 µm or larger. Japanese Patent Kohyo Publication No. H9-507049 teaches a dry type preparation method for a dry powder inhalation, but the method requires sieving once to remove fine powders from the carrier particle surface and it also calls for pulverizing the carrier particles by a ball mill.

Accordingly, it is an object of this invention to provide a dry powder inhalation of the type in which a pharmaceutically active ingredient is adhered to the surface of the carrier, that provides reduced adhesion-agglomeration tendencies during storage, that exhibits a high delivery fraction of the active ingredient to the lower respiratory tract, such as bronchiole and the like, that adheres less during inhalation to the powder dispersion device, that disperses well in the gas phase, and that has good inhalation capability.

It is another object of this invention to provide said dry powder inhalation with improvements during inhalation as to the taste and sense of discomfort in the oral cavity or the throat.

It is a further object of this invention to provide a preparation method which requires no complicated processes for readily preparing said dry powder inhalation in a simple manner.

DISCLOSURE OF THE INVENTION

As a result of extensive studies of a way to solve the above problems, the present inventors discovered that the above problems can be overcome by improving respectively on the carrier and the active ingredient to be adhered thereto and the like substance, for a dry powder inhalation wherein at least a micronized active ingredient is adhered to the surface of a carrier particle and by utilizing, as carrier particles, a variety of sweet tasting components that have been practically used in therapeutic pharmaceuticals, thereby developing a dry powder inhalation with improved taste, even when in particular, a very bitter active ingredient is used; which discovery led to completion of the present invention. The above problems were also found to be overcome by preparing said dry powder inhalation by a dry type preparation method without using any solvent, which has led to the completion of this invention.

That is, the present invention is a dry powder inhalation wherein at least a micronized pharmaceutically active ingredient is adhered to the surface of a carrier particle and wherein the carrier particle is erythritol and/or trehalose.

That is, the present invention is a dry powder inhalation wherein at least a micronized pharmaceutically active ingredient and a micronized surface modifier are adhered to the surface of a carrier particle and wherein the carrier particle is one, two, or more selected from the group consisting of erythritol, trehalose, and lactose.

These materials provide a dry powder inhalation with a minimal tendency for adhesive-agglomerative property during storage and which has an excellent state of dispersion. The dry powder inhalation is of the type which adheres less during inhalation to the powder dispersion device, which disperses well in the gas phase, and which exhibits a high delivery fraction of the active ingredient to the lower respiratory tract such as the bronchiole and the like. Furthermore, the dry powder inhalation of this invention, using erythritol or trehalose, improves on the taste or discomfort in the oral cavity and throat even with a very bitter tasting active ingredient, thereby making it easy to inhale for intake, so that the invention makes it particularly easy for administration to patients, in particular the pediatric and the elderly patient, so as to find a suitable use for treatment and prevention of disease.

In the dry powder inhalation wherein at least a micronized pharmaceutically active ingredient and a micronized surface modifier are adhered to the surface of a carrier, the carrier particles in the present invention may be erythritol and the micronized surface modifier may be lactose and/or trehalose.

In addition, in the dry powder inhalation wherein at least a micronized pharmaceutically active ingredient and a micronized surface modifier are adhered to the surface of a carrier, the carrier particle may be trehalose and the micronized surface modifier may be lactose and/or trehalose.

Further, in the dry powder inhalation wherein at least a micronized pharmaceutically active ingredient and a micronized surface modifier are adhered to the surface of a carrier, the carrier particle in the present invention may be lactose and the micronized surface modifier may be lactose and/or trehalose.

These can particularly obtain the effects of the foresaid invention effectively.

It is particularly effective for the dry powder inhalation of this invention to use for the active ingredients, S-36496 and/or Pralmorelin dihydrochloride, which may be used as a micronized active ingredient for a dry powder inhalation wherein at least the micronized pharmaceutically active ingredient is adhered to the surface of a carrier. Furthermore, it can also be used as a micronized active ingredient for any of the above-mentioned dry powder inhalations.

Use of these active ingredients permits a dry powder inhalation formulation to function effectively, thereby achieving the full effect of the present invention.

In the dry powder inhalation of this invention, the carrier particles preferably have a mean particle diameter of 30–1501 μm and the micronized active ingredient a mean particle diameter of 1–6 μm. In the dry powder inhalation of this invention, the micronized surface modifier should preferably have a mean particle diameter of not more than 3 μm.

Use of materials having these particle sizes will further effectively realize the effects of the present invention.

In the dry powder inhalation of this invention, it is preferred for the content of the carrier particles to be 79.9–99% by weight of the total weight of the dry powder inhalation, and the content of the micronized active ingredient to be 0.01–20% of the total weight of the dry powder inhalation for fully providing the effects of this invention.

Furthermore, in the dry powder inhalation of this invention, the content of the micronized surface modifier should preferably be 0.1–2% of the total weight of dry powder inhalation for fully providing the effects of this invention.

It is preferred for the dry powder inhalation of this invention to have enough flowability to be filled into capsules for fully realizing the effects of the present invention.

The present invention is also a method for preparing a dry powder inhalation, which comprises mixing a micronized active ingredient with core particles, optionally along with a micronized surface modifier, and carrying out a dry type coating. It is preferred to prepare the micronized active ingredient and micronized surface modifier using a dry type pulverizer. The dry pulverizer is preferably an air jet mill.

In the preparation method for the dry powder inhalation of this invention, it is preferred for the entire processes of pulverization, mixing, and coating to be carried out as a dry method.

According to these preparation processes, without using wet pulverization, spray drying, freeze drying or a like method or using liquid antistatic agents and the like that have been essential in conventional preparation methods, it is now possible to generate a directly capsule-fillable dry powder inhalation using a simple method of preparation made possible with common apparatus, which calls for covering the carrier particles via dry coating with a micronized active ingredient, optionally along with a micronized surface modifier, thereby generating a powder that has enough flowability to be capsule-fillable. According to this invention, a dry method can be used for the preparation, which is highly suitable for solvent-unstable active ingredients.

Furthermore, the dry powder inhalation of this invention is filled into a capsule and is utilized as a capsulated medication using an inhaler device.

On charging the capsulated medication into an inhalation device and inhaling through the inhaler device, the active ingredient adhered to the surface of carrier particles will rapidly be redispersed thereby causing the active ingredient to reach down efficiently into the lower respiratory tract such as the bronchiole.

The term "average particle size" in this invention represents the size of particles corresponding to the 50% level in a particle size distribution.

The surface modifier used in this invention is adhered to the surface of carrier particles along with a micronized active ingredient and it acts to prevent the agglomeration or electrification of the dry powder inhalation where at least the micronized active ingredient is adhered to the surface of the carrier particles.

Best Embodiments for Carrying out the Present Invention

Hereafter, embodiments of this invention are described in detail.

1. Carrier Particles

The carrier particles in this invention become core particles to which at least a micronized active ingredient, preferably at least a micronized active ingredient and a micronized surface modifier are adhered.

The carrier particles used in this invention include, for example, erythritol, trehalose, lactose, and the like. One, two, or more carrier particles are selected in this invention.

From among these carrier particles, erythritol and trelalose are minimally hygroscopic and are at low risk of adhesion and agglomeration or caking or deliquescence during the preparation and during storage. In addition, they are sweet in taste so that when a dry powder inhalation using such carrier particles is inhaled, the sweetness of the carrier particles deposited in the oral cavity or the throat will mitigate the bitterness of the active ingredient, thereby facilitating its administration to pediactric and elderly patients. Accordingly, the above materials are preferably used as nucleus particles for adhering at least a micronized active ingredient or for adhering at least a micronized active ingredient and a micronized surface modifier.

Among these carriers particles, lactose is preferred. When at least a micronized active ingredient and a micronized surface modifier are adhered to such a carrier particle, one can take advantage of the properties of lactose: minimal moisture absorption and minimal adhesion-agglomeration during storage.

In the use of carrier particles, any one, two, or more may be selected from the corresponding carrier particles.

2. Active Ingredient

The active ingredient in this invention is micronized and adhered to the surface of carrier particles, preferably along with the micronized surface modifier.

The active ingredients used in this invention include one, two, or more selected from anti-leuokotriene agents, anti-thromboxane agents, anti-inflammatory agents, anti-infectives, antihistamines, anti-asthmatics, antitussives, expectorants, bronchodilators, antiallergics, anti-tuberculosis agents, antianginal agents, analgesics, peripheral and cerebral vasodilators, antiemetics, antifungals, short statue treatment agents, and the like.

The active ingredients are, for example, anti-leukotriene/anti-thromboxane agents such as 2-{N-[4-(4-chlorobenzenesulfonylamino)butyl]-N-{3-[(4-isopropyl-2-thiazoyl)methoxy]benzyl}}sulfamoylbenzenolic acid (hereafter "S-36496" represented by (as) Compound No. 1 described in Example 11 of WO98/57935 and the like); anti-inflammatory agents such as Beclomethasone, prednisolone; antihistamine agents such as diphenhydramine, chlorpheniramine maleate, triprolidine, and the like; antitussives such as codeine phosphate, Noscapine, methyl ephedrine hydrochloride, and the like; expectorants such as Ambroxol, bromohexine hydrochloride, acetylcisteine, and the like; brochlodilators such as Mabuterol hydrochloride, isoproterenol hydrochloride, Orciprenaline, Salbutamol, Tulobuterol, Trimetoquinol, ipratropium bromiode and oxytropium bromide, and the like; antiallergics such as sodium cromoglicate, Amlexanox, tranilast, and the like; anti-tuberculosis drugs such as Ethanbutol hydrochloride, Rifambicin, and the like; anitanginal agents such as phenylpropanolamine hydrochloride, bupranolol hydrochloride; nitroglycerin, Isosorbide nitrate, Pindlol, Propanolol hydrochloride, and the like; peripheral and cerebral vasodialators such as Beraprost sodium; antifungals such as Butenafine hydrochloride; drugs for treating short stature, such as Pralmorelin and Pralmorelin dihydrochloride and the like described in WO93/04081 as GHRP-2.

From among these active ingredients, the present invention is particularly effective to use S-36496 and/or pralmoreline dihydrochloride in the form of a dry powder inhalation.

The preferred embodiment in adhering an active ingredient to the surface of carrier particles includes a dry powder inhalation where at least micronized S-36946 and/or pralmorelin dihydrochloride along with a micronized surface modifier is adhered to the surface of one, two, or more carrier particles selected from the group consisting of erythritol, trehalose, and lactose.

The active ingredients may be diluted with a diluent, of a type generally used in the food and drug fields.

For further improvement in the taste and the flavor of the active ingredients, it is possible to add a sourness agent, a sweetening agent, and flavors. The sourness agents include, for example, citric acid, tartaric acid, malic acid, adipic acid, and the like. The sweetening agents include, for example, sodium saccharin, glucose, and the like. Aromatic flavors can be used and include, for example, lemon, orange, grapefruit, grape, menthol, spearmint, peppermint, vanilla, cinnamon, and the like flavors One, two or more of these taste and flavor enhancement agents may be added at an appropriate time and in appropriate amounts, for example, during the time of mixing of the active ingredient and the surface modifier or during the dry coating process.

3. Surface Modifiers

It is preferred to use a surface modifier in this invention. The surface modifier is adhered to the surface of carrier particles along with active ingredients, and functions as an anti-agglomerative and an antistatic agent for the active ingredients and carrier particles. It is preferred for the surface modifier not to cause any adverse effect such as degradation of the active ingredients, and to be a water soluble additive which has a track record of use in dry powder inhalation. Such surface modifiers include lactose, trehalose, and the like.

Any one, two or more members from these surface modifiers are selected in this invention. With respect to lactose, if it is necessary to differentiate the lactoses between the carrier particle lactose and the surface modifier lactose, they are called the carrier lactose and the adherer lactose. This is also the same for the trehalose, namely one is called the carrier trehalose and the other is the adherer trehalose.

4. Dry Powder Inhalation

A particularly preferred embodiment for the dry powder inhalation of this invention is one wherein at least a micronized pharmaceutically active ingredient and a micronized surface modifier are adhered to the surface of a carrier particle.

A further preferred embodiment for the dry powder inhalation is one wherein the carrier particle is one, two, or more selected from the group consisting of erythritol, trehalose, and at least a micronized pharmaceutically active ingredient and a micronized surface modifier are adhered to the surface of the carrier particle.

These preferred embodiments are, for example:

(1) A dry powder inhalation wherein at least a micronized pharmaceutically active ingredient and a micronized lactose and/or trehalose is adhered to the surface of a carrier particle comprised of erythritol.

(2) A dry powder inhalation wherein at least a micronized pharmaceutically active ingredient and a micronized lactose and/or trehalose is adhered to the surface of a carrier particle comprised of trehalose.

(3) A dry powder inhalation wherein at least a micronized pharmaceutically active ingredient and a micronized lactose and/or trehalose is adhered to the surface of a carrier particle comprised of lactose. Further preferred embodiments are specifically, for example:

(1) A dry powder inhalation wherein at least a micronized S-36496 and/or pralmoreline dihydrochloride and a micronized lactose and/or trehalose is adhered to the surface of a carrier particle comprised of erythritol.

(2) A dry powder inhalation wherein at least a micronized S-36496 and/or pralmoreline dihydrochloride and a micronized lactose and/or trehalose is adhered to the surface of a carrier particle comprised of trehalose.

(3) A dry powder inhalation wherein at least a micronized S-36496 and/or pralmoreline dihydrochloride and a micronized lactose and/or trehalose is adhered to the surface of a carrier particle comprised of lactose.

It is preferred that the dry powder inhalation has good flowability. Improved flowability permits capsule filling with reduced levels in mass variation and mass deviation, which also facilitates a smooth mass production system for capsule filling. It also can prevent re-agglomeration of the medication. Flowability is measured by allowing said medication to gently fall to pile up and measuring the slant angle made between the horizontal plane and the pile. This slant angle is called the angle of repose. For example, if the carrier particle is erythritol, the angle of repose of the preparation is not more than 45°, preferably not more than 42°, which will mean sufficient flowability so as to be directly fillable into capsules and will enable the re-agglomeration of said mixture to be prevented. If the carrier particle is trehalose, the angle of repose of the preparation should not be more than 41°, preferably not more than 40°. The lower limit for the angle of repose is preferably 35°.

5. On Particle Sizes of Carrier Particles, Active Ingredients, and Surface Modifiers The carrier particles in this invention should normally have a mean particle diameter of 30–150 µm, preferably 50–90 µm, in particular about 80 µm.

The particle size of the active ingredient is reduced by micronization to a mean particle diameter in the range of 1–6 µm, particlularly 1–3 µm from the standpoint of inhalability.

The surface modifier should preferably have a mean particle diameter of not more than 3 m, particularly 0.1–3 µm. It is further preferred to be 1–2 µm, in particular, 1.5 µm.

6. On the Contents of Carrier Particles, Active Ingredients, and Surface Modifiers The carrier particle contents should preferably be 79.9–99% of the total weight of a dry powder inhalation.

The micronized active ingredient contents, although differing depending upon the active ingredient type, should preferably be 0.01–20% of the total weight of dry powder inhalation.

The micronized surface modifier contents, differing depending upon the type and amount of the active ingredient added, which is the other component adhered to the surface of carrier particles, are preferably 0.1–2.0% of the total weight of the dry powder inhalation, more particularly, in the range of 0.5–1.0% by weight thereof. If multiple surface modifiers are used, the total amount should be held at 0.1–2.0% of the total weight of dry powder inhalation.

7. On the Preparation of Dry Powder Inhalation

The preparation of a dry powder inhalation of this invention is described below. For micronization of the active ingredient and surface modifier to be adhered to the surface of the carrier particles, a common apparatus such as a dry pulverizer is used, for example, a driven-container media mill, agitated media mill, and the like. Specifically, one may use a jet mill, a hammer mill, a pin mill, a turbo mill, a super micron mill, a tumbling ball mill, a vibration ball mill, a satellite mill, a centrifugal fluidization mill, and the like. From among these, a jet mill is preferred.

Adhering the micronized active ingredient, optionally, with the micronized surface modifier, to the surface of carrier particles, preferably is carried out by dry coating. That is, the micronized active ingredient and carrier particles, optionally along with a micronized surface modifier, are mixed and then dry coated. It is preferred to premix the micronized surface modifier with carrier particles before the addition of the active ingredient.

Dry coating is carried out using a conventional apparatus used for the preparation of pharmaceutical preparations, for example, using a surface modification apparatus modifier device, a high speed mixer, a high speed agitation type mixing granulator, a universal kneader, and the like. Specifically, a dry powder inhalation is prepared by dry coating using Mechanomill (manufactured by Okada Seiko Co., Ltd.), Vertical-Granulator (manufactured by Powrex Corp.), High-speed-Mixer (Fukae Kogyo KK), Hybridizer and Laboratory-Matrix (manufactured by Nara Machinery Co., Ltd.), Theta-Composer (manufactured by Tokuju Kosakusho Co., Ltd.).

Changing the mixing time in the dry coating enables one to adjust the adhesive force of the active ingredient to the surface of carrier particles, whereby one can adjust inhalation efficacy of the active ingredient toward the lower respiratory tracts. Optionally, a two-step method may be used whereby the carrier particles and micronized surface modifier are mixed in a first process and then the mixture is mixed with the active ingredient in the second process.

It is preferred to carry out the entire processes of pulverization, mixing, and coating by dry processing without using any solvent at all.

8. Use Configuration of Dry Powder Inhalation

The dry powder inhalation of this invention is filled into a capsule, resulting in a capsulated form, which can then be inhaled from an inhaler device. For filling the capsule, an apparatus commonly used for filling powders or fine granules or granules into capsules may be used. For example, one may employ, for the filling mechanism, an auger types a disk type, a compression type, a die-compression type, a press type, a dribble type, a double slide type, a slide piston type, a continuous type, a vacuum type, and the like mechanisms. It is preferred to use a suitable one from among these mechanisms where the filled volume of the dry powder inhalation in a capsule should preferably be ⅕–½ of the capsule volume.

For the above capsule base, one may use a hard capsule base described in the Japan Pharmacopoeia General Rule for Preparations "Capsules"; however, the preferred capsule base to be filled with the micronized dry powder inhalation is one that resists an electrostatic adherence, and further, is a minimally hygroscopic capsule base. The preferred capsule base is hydroxypropylmethyl cellulose.

One may use a commercial inhaler device for a dry powder inhalation containing the dry powder inhalation filled in a capsule, such as a Jethaler, Spinhaler, Rotahaler, Cyclohaler, Inhaler M (all are registered trade names) and the like. The selection is made so that the active ingredient particles can be uniformly dispersed in the gas phase to permit the active ingredient in the capsule to be rapidly inhaled by virtue of the unfilled portion of the capsule container and the device. Optionally, instead of a capsule, the dry powder inhalation may be filled in a blister or reservoir for inhalation of the active ingredient from the device. (Pharmacia, Voluime 33, No. 4, p. 376 (1997)

(Kopna No. 16, p. 7, Dispersion and Characterization of Pharmaceutical Dry Powder Aerosols (1998).

However, for practicality, it is particularly preferred to use an inhaler device which can be readily disassembled and cleaned, and easily assembled.

The present invention is further explained in detail using the following examples: Percentages (%) unless otherwise noted are mass percentages.

EXAMPLE 1

For the objective of selecting a material suitable as the carrier for a dry powder inhalation, moisture absorption tests were performed on erythritol, xylitol, lactose, D-mannitol, Amalty, glucose, Stevia, Benecoat and aspartame. They showed erythritol to be the least hygroscopic and to have optimum properties as a carrier for a dry powder inhalation. (Tables 1, 2, and 3)

TABLE 1

Tests Results for Hygroscopic Properties
(Storage Conditions: 25° C., Humidity 60%)

| Test Carrier | % Moisture Absorption | | | |
|---|---|---|---|---|
| | 24 Hours | 72 Hours | 168 Hours | 366 Hours |
| Erythritol | 0.000 | 0.000 | 0.000 | 0.000 |
| Xylitol | 0.000 | 0.000 | 0.019 | 0.021 |
| Lactose 325M | 0.000 | 0.000 | 0.000 | 0.000 |

TABLE 2

Test Results for Hygroscopic Properties
(Storage Conditions: 25° C., Humidity 75%)

| Test Carrier | % Moisture Absorption | | | | |
|---|---|---|---|---|---|
| | 24 Hours | 48 Hours | 72 Hours | 168 Hours | 336 Hours |
| Erythritol | 0.008 | 0.011 | 0.014 | 0.010 | 0.012 |
| D-Mannitol | 0.019 | 0.019 | 0.019 | 0.028 | — |
| Xylitol | 0.087 | 0.104 | 0.126 | 0.124 | 0.126 |
| Amalty | 0.478 | 1.138 | 1.171 | 1.252 | — |
| Glucose | 0.406 | 0.902 | 1.922 | 4.998 | — |
| Stevia | 0.636 | 1.396 | 3.260 | 3.260 | — |
| Benecoat | 4.180 | 4.850 | 6.331 | 6.637 | — |
| Aspartame | 6.539 | 10.877 | 10.985 | 11.163 | — |
| Lactose 325M | 0.029 | — | 0.031 | 0.033 | 0.031 |

—: Not measured

TABLE 3

Test Results for Hygroscopic Properties
(Storage Conditions: 25° C., Humidity 90%)

| Test Carrier | % Moisture Absorption | | | | |
|---|---|---|---|---|---|
| | 16 Hours | 24 Hours | 48 Hours | 72 Hours | 168 Hours |
| Erythritol | — | 0.055 | 0.070 | 0.070 | 0.070 |
| D-Mannitol | 0.539 | 0.672 | 0.806 | 0.916 | 1.122 |
| Xylitol | — | 3.796 | 17.917 | x | x |
| Amalty | 0.775 | 0.971 | 2.513 | 3.373 | 8.391 |
| Glucose | 0.308 | 0.680 | 3.568 | 7.109 | 10.500 |
| Stevia | 0.276 | 2.521 | 4.565 | 8.541 | 8.869 |
| Benecoat | 2.757 | 6.574 | 7.815 | 9.856 | 11.233 |

TABLE 3-continued

Test Results for Hygroscopic Properties
(Storage Conditions: 25° C., Humidity 90%)

| Test Carrier | % Moisture Absorption | | | | |
|---|---|---|---|---|---|
| | 16 Hours | 24 Hours | 48 Hours | 72 Hours | 168 Hours |
| Aspartame | 10.476 | 10.741 | 11.448 | 11.521 | 11.749 |
| Lactose 325M | — | 0.094 | — | 0.090 | 0.092 |

—: Not measured
x: Not possible to measure (because the samples deliquesced.)

Erythritol: Nikken Kagaku Kogyo KK
D-Mannitol: Kyowa Hakko Kogyo Co., Ltd.
Xylitol: Eisai Co., Ltd.
Amalty: To a Kasei Kogyo KK
Glucose: Otsuka Pharmaceutical Co., Ltd.
Stevia: Dainippon Ink and Chemicals, Incorporated
Benecoat: Kao Corporation
Aspartame: AJINOMOTO Co., Inc.
Lactose 325M: DMV Company

EXAMPLE 2

In order to ascertain that trehalose is a material having properties suitable as a carrier for dry powder inhalations, it was compared to lactose, a well-known carrier for dry powder inhalation. A test was carried out for comparing hygroscopicity. The trehalose used was the product of Asahi Kasei Kogyo KK, and Lactose 325M from the DMV Company. As a result, trehalose was only slightly hygroscopic with about the same properties as those of lactose; thus it was confirmed that the trehalose can be used as a carrier for a dry powder inhalation. (Table 4, 5)

TABLE 4

| Test Carriers | % Moisture Absorption | | | |
|---|---|---|---|---|
| | 24 Hours | 72 Hours | 168 Hours | 366 Hours |
| Trehalose | 0.000 | 0.000 | 0.000 | 0.000 |
| Lactose 325M | 0.000 | 0.000 | 0.000 | 0.000 |

(Storage condition: 25° C., Humidity 60%)

TABLE 5

| Test Carrier | % Moisture Absorption | | | | |
|---|---|---|---|---|---|
| | 16 Hours | 24 Hours | 48 Hours | 72 Hours | 168 Hours |
| Trehalose | — | — | 0.008 | 0.023 | 0.020 |
| Lactose 325M | 0.029 | — | 0.031 | 0.033 | 0.031 |

(Storage condition: 25° C., Humidity 75%)
—: Not measured

EXAMPLE 3

Surface modifiers were studied with the objective of preventing the agglomeration and improving the flowability of dry powder inhalations. The experiments were carried out with erythritol (mean particle diameter: 59 µm) as carrier particles along with 1 mass % of a surface modifier per 100% of the carrier particles, by measurement of the angle of repose and visually inspecting the extent of powder agglomeration (Table 6). As a result, it was shown that lactose having a mean particle diameter of 1.5 μm was most useful for preventing the agglomeration and improving flowability.

TABLE 6

Relationships Between the Added Amount of Surface Modifiers and Flowability

| Component (Added Amount 1%) | Angle of Repose | Result of Visual Observation |
|---|---|---|
| No surface modifier added | 60° | Agglomerates |
| Erythritol (mean particle diameter = 1.5 μm | 60° | No improvement for the mixed powder. |
| Lactose (mean particle diameter = 1.5 μm) | 43° | Essentially no tendency for the mixed powder to agglomerate |
| Lactose (mean particle diameter = 10 μm) | 48° | Some tendency for the mixed powder to agglomerat |
| Lactose (mean particle diameter = 15 μm) | 52° | Some tendency for the mixed powder to agglomerate |
| Lactose (mean particle diameter = 30 μm) | 55° | No improvement for the mixed powder. |
| Lactose (mean particle diameter = 65 μm) | 56° | No improvement for the mixed powder |

EXAMPLE 4

Surface modifiers were studied with the objectives of preventing the tendency for the carrier trehalose particles for dry powder inhalation to agglomerate and of improving their flowability. Experiments were carried out with carrier trehalose having an a mean particle diameter of 81 μm [the product obtained by sieving with two sieves: 45 μm (330 mesh sieve) and 106 μm (140 mesh sieve)], along with addition of 1% of a surface modifier based on 100% of the carrier trehalose, by measuring the angle of repose and judging the extent of agglomeration of the preparation by visual inspection (Table 7).

As a result, it was found that a trehalose fine powder micronized to an mean particle diameter of 1.4 μm was found to be useful for preventing agglomeration and for improving flowability in a manner similar to that of the lactose fine powder (mean particle diameter 1.5 μm), suggesting that if trehalose is used as a carrier particle, both micronized trehalose and lactose can be used as a surface modifier.

TABLE 7

| Surface Modifiers | Angle of Repose | Result of Visual Observation |
|---|---|---|
| No addition of surface modifier | 42° | Some electrostatic adhesion observed. |
| Trehalose (mean particle diameter = 1.4 μm) | 39° | No tendencies observed for the mixed powder to agglomerate; and electrostatic adhesion improved. |
| Trehalose (mean particle diameter = 13 μm) | 40° | No tendencies observed for the mixed powder to agglomerate; but some over electrostatic adhesion observed. |
| Lactose (mean particle diameter = 1.5 μm) | 40° | No tendencies observed for the mixed powder to agglomerate; and electrostatic adhesion improved. |

EXAMPLE 5

A lactose micronized by a jet mill (mean particle diameter: 1.5 μm) and carrier particles (mean particle diameter: 54 μm) were premixed to which mixed powder was added S-36496 at the formulation given in the Table 8 below, followed by dry coating for a dry type coating time of 10 minutes using a Mechanomill (manufactured by Okada Seiko KK, 10 g scale). The prepared dry powder inhalation was observed with a scanning electron microscope (ABT-55 Topcon Corp.), which indicated that the micronized active ingredient and lactose uniformly adhered around the carrier particles.

TABLE 8

Formulation

| Component | Composition |
|---|---|
| S-36496 | 10% |
| Micronized Lactose | 1% |
| Erythritol | 89% |

EXAMPLE 6

A lactose micronized by a jet mill (mean particle diameter: 1.5 μm), 1%, and carrier trehalose particles (mean particle diameter: 81 μm), 98% were premixed to which mixed powder was added S-36496, 1%, followed by dry coating for 10 minutes using a Mechanomill (Okada Seiko KK, 10 g scale) to prepare a dry powder inhalation. The prepared dry powder inhalation was observed with a scanning electron microscope (ABT-55 Topcon Corp.), which indicated that the micronized active ingredient and lactose were uniformly adhered around the carrier trehalose particles.

EXAMPLE 7

In order to study the optimum particle size of erythritol suitable for dry powder inhalations, the micronized lactose (mean particle diameter: 1.5 μm) and carrier particles with three different particle sizes were added and pre-mixed according to the formulation given in Table 9 below, after which S-36496 was added and was dry coated using a Mechanomill (Okada Seiko KK) (10 g scale). Each of the prepared dry powder inhalations was filled in a capsule to carry out an in vitro study of a lung delivery fraction, where the optimum carrier particle size was selected. The experiments were carried out in accordance with the measurement method using a multi-stage cascade impactor described in the United States Pharmacopeia (USP23), page 1763 (1995).

Capsulated preparations (The Japanese Pharmacopeia No. 2 HPMC capsules: manufactured by Shionogi Qualicaps Co. Ltd) which were filled with about 40 mg each of three dry powder inhalations were prepared and mounted on an inhaler device (Jethaler; Unisia Jecs Corp.) The Jethaler was then attached to the mouthpiece of a cascade impactor (Andersen sampler; Model AN-200) and inspired at a flow rate of 28.3 L/min., thereby dispersing the micronized preparation in the capsule and measuring the residual active ingredient in the capsule and in the inhaler device as well as the distribution of the active ingredient at each stage, using liquid chromatography. The results are given in Table 10. It was confirmed that in the in vitro test with cascade impactor, the lung delivery fraction at stages 2–7 corresponding to the respiring fraction differed substantially depending on the different carrier particles. The results of Table 10 show that the carrier particles with erythritol used for dry powder inhalations are found to be optimum at a mean particle diameter of about 80 μm.

TABLE 9

Formulation

| Component | Composition | | |
|---|---|---|---|
| S-36496 | 10% | 10% | 10% |
| Micronized lactose | 1% | 1% | 1% |
| Erythritol (mean particle diameter = 53.8 μm) | 89% | — | — |
| Erythritol (mean particle diameter = 81.6 μm) | — | 89% | — |
| Erythritol (mean particle diameter = 155.9 μm) | — | — | 89% |

TABLE 10

Results of in vitro Test

| Results of in vitro Test | (Unit, %) | | |
|---|---|---|---|
| mean particle diameter (μm) of the carrier particles | 53.8 | 81.6 | 155.9 |
| Capsule | 3.0 | 2.6 | 2.5 |
| Inhaler device | 18.2 | 14.6 | 2.9 |
| Throat | 22.0 | 16.9 | 1.7 |
| Stage 0 | 28.9 | 21.8 | 66.4 |
| Stage 1 | 3.5 | 3.8 | 15.2 |
| Stages 2–7 | 24.4 | 40.4 | 11.3 |

EXAMPLE 8

In order to study the optimum particle size of erythritol suitable for dry powder inhalations, the micronized lactose (mean particle diameter: 1.5 μm), 1 mass %, and trehalose carrier particles with three different particle size levels (mean particle diameter: 81.0 μm, 97.9 μm, 48.6 μm), 89%, were added and pre-mixed, after which S-36496, 10%, was added and was dry coated using a Mechanomill (manufactured by Okada Seiko KK) (10 g scale). Each of the prepared three dry powder inhalations was filled in a capsule to carry out an in vitro study of a lung delivery fraction. The experiments were carried out in accordance with the measurement method using a multi-stage cascade impactor described in the United States Pharmacopeia (USP23), page 1763 (1995).

Capsulated preparations (The Japanese Pharmacopeia No. 2 HPMC capsules: manufactured by Shionogi Qualicaps Co., Ltd.) which were filled with about 40 mg each of three dry powder inhalations were prepared and mounted on an inhaler device (Jethaler; Unisia Jecs Corp.) The Jethaler was then attached to the mouthpiece of a cascade impactor (Andersen sampler Model AN-200) and inspired at a flow rate of 28.3 L/min., thereby dispersing the micronized medication in the capsule and measuring the residual active ingredient in the capsule and in the inhaler device as well as the distribution of the active ingredient at each stage with liquid chromatography. The results are given in Table 11. It was confirmed that in the in vitro test with cascade impactor, the lung delivery fraction at stages 2–7 corresponding to the respiring fraction differed substantially depending on the different carrier particles. The results of Table 11 show that the trehalose carrier particles used for dry powder inhalations were found to be optimum at a mean particle diameter of about 80 μm.

TABLE 11

| Particle size of Carrier trehalose | Residual and Distributed Fractions of Active Ingredient S-36496 | | |
|---|---|---|---|
| | 81.0 μm | 97.9 μm | 48.6 μm |
| Capsule | 4.9% | 5.8% | 9.0% |
| Inhaler device | 19.1 | 25.1 | 24.2 |
| Throat | 24.2 | 27.2 | 32.8 |
| Stage 0 | 18.4 | 18.2 | 24.7 |
| Stage 1 | 2.0 | 5.8 | 2.9 |
| Stages 2–7 | 31.4 | 17.9 | 6.4 |

EXAMPLE 9

Jet mill micronized lactose (mean particle diameter: 1.5 μm) and carrier trehalose particles (mean particle diameter: 81 μm) similar to Example 4 were premixed according to the formulation given in Table 12 below, followed by adding S-36496 to the powdered mixture and dry coating using a Mechanomill (Okada Seiko KK) (10 g scale). The prepared dry powder inhalations were measured with liquid chromatography for the contents of the adhered S-36496, which confirmed a uniform adherence and dispersion of the active ingredient. (Table 13) The values in Table 13 show the fractions with respect to the amount of S-36496 added at dry coating as 100%. A similar observation was made using a scanning electron microscope (ABT-55 Topcon Corp.), which confirmed a uniform adherence of micronized active ingredient and lactose around the carrier particles.

Capsulated preparations (The Japanese Pharmacopeia No. 2HPMC capsules: manufactured by Shionogi Qualicaps Co., Ltd.), which were filled with about 40 mg each of three dry powder inhalations, were prepared and mounted on an inhaler device (Jethaler®; Unisia Jecs Corp.). The Jethaler® brand device was then attached to the mouthpiece of a cascade impactor (Andersen sampler; Model AN-200) and inspired at a flow rate of 28.3 L/min., thereby dispersing the dry powder inhalation in the capsule and measuring the residual active ingredient in the capsule and in the inhaler device as well as the distribution of the active ingredient at each stage with liquid chromatography. The results are given in Table 14. The in vitro test with cascade impactor showed that the three prepared dry powder inhalations gave the same level for the delivery fractions for stages 2–7 in all preparations regardless of the amount of the active ingredient added, suggesting that a combination of the carrier trehalsose and the preparation method of this invention enables a good dry powder inhalation to be prepared regardless of the active ingredient concentration.

TABLE 12

| | Mixture Ratio (%) | | |
|---|---|---|---|
| | Sample No. 1 | Sample No. 2 | Sample No. 3 |
| S36496 | 3.0% | 5.0% | 10.0% |
| Micronized Lactose | 1.0 | 1.0 | 1.0 |
| Carrier Trehalose | 96.0 | 94.0 | 89.0 |

TABLE 13

Contents of Adhered Active Ingredient S-36496 (%)

| Sample No. 1 | Sample No. 2 | Sample No. 3 |
|---|---|---|
| 95.2% | 96.0% | 95.8% |

TABLE 14

Residual and Distributed Fractions of Active Ingredient S-36496

|  | Sample No. 1 | Sample No. 2 | Sample No. 3 |
|---|---|---|---|
| Capsule | 5.8% | 6.4% | 5.9% |
| Inhaler device | 18.8 | 20.2 | 20.1 |
| Throat | 16.7 | 16.4 | 14.8 |
| Stage 0 | 24.5 | 22.8 | 23.9 |
| Stage 1 | 7.3 | 5.4 | 7.2 |
| Stages 2–7 | 26.9 | 28.8 | 28.1 |

EXAMPLE 10

Lactose micronized by a jet mill (mean particle diameter: 1.5 μm) and carrier lactose particles (Lactose 325 M, manufactured by DMV Co.; mean particle diameter 65.5 μm) were prepared according to the formulation given in Table 15 below, followed by adding S-36496 (mean partricle diameter: 1.6 μm) to the powdered mixture and dry coating using a Mechanomill (Okada Seiko KK) (15 g scale). The prepared dry powder inhalation was observed with a scanning electron microscope (ABT-55, Topcon Corp.), which confirmed the uniform adherence of micronized active ingredient and the adhering lactose around the carrier particles.

A capsulated preparation (The Japanese Pharmacopeia No. 2HPMC capsules: manufactured by Shionogi Qualicaps Co., Ltd.) which was filled with about 40 mg of the prepared dry powder inhalations was prepared and mounted on an inhaler device (Jethaler; Unisia Jecs Corp.) The Jethaler was then attached to the mouthpiece of a cascade impactor (Andersen sampler; Model AN-200) and inspired at a flow rate of 28.3 L/min., thereby dispersing the dry powder inhalation in the capsule and measuring the residual active ingredient in the capsule and in the inhaler device as well as the distribution of the active ingredient at each stage with liquid chromatography. The results are given in Table 16.

TABLE 15

| | Ration of Mixture % |
|---|---|
| S-36496 | 3.2 |
| Carrier Lactose | 95.8 |
| Micronized Lactose | 1.0 |

TABLE 16

Residual and Distributed Fractions of Active Ingredient S-36496 (%)

| Capsule | 8.2 |
|---|---|
| Inhaler device | 19.3 |
| Throat | 25.7 |
| Stage 0 | 19.5 |
| Stage 1 | 9.1 |
| Stages 2–7 | 18.2 |

EXAMPLE 11

Lactose micronized by a jet mill (mean particle diameter: 1.5 μm) and carrier erythritol particles (mean particle diameter: 80.8 μm) were prepared according to the ratios given in Table 17 below, followed by adding micronized Pralmorelin dihydrochloride described in Japanese Patent Kohyo Publication No. H7-507039 (mean particle diameter: 1.9 μm) to the powdered mixture and dry coating using a Mechanomill (Okada Seiko KK). The prepared dry powder inhalation was observed with a scanning electron microscope (ABT-55 Topcon Corp.), which confirmed the uniform adherence of micronized active ingredient and lactose around the carrier particles.

A capsulated preparation (The Japanese Pharmacopeia No. 2HPMC capsules: manufactured by Shionogi Qualicaps Co., Ltd.), which was filled with about 40 mg of three dry powder inhalations, were prepared and mounted on an inhaler device (Jethaler®; Unisia Jecs Corp.). The Jethaler® brand device was then attached to the mouthpiece of a cascade impactor (Andersen sampler; Model AN-200) and inspired at a flow rate of 28.3 L/min., thereby dispersing the dry powder inhalation in the capsule and measuring the residual active ingredient in the capsule and in the inhaler device as well as the distribution of the active ingredient at each stage with liquid chromatography. The results are given in Table 18. Even after storage for two months in glass bottles containing silica gel at 40° C. and 25° C., this preparation indicated essentially no change in the fractions of the drug distributed.

TABLE 17

| | Ratio of Mixture % |
|---|---|
| Pralmorelin Dihydrochloride | 5.0 |
| Carrier Erythritol | 93.5 |
| Micronized Lactose | 1.5 |

TABLE 18

Residual and Distributed Fractions of Active Ingredient Pralmorelin dihydrochloride (%)

| Capsule | 3.6 |
|---|---|
| Inhaler device | 11.5 |
| Throat | 13.5 37.1 |
| Stage 0 | 7.7 |
| Stage 1 | 26.6 |
| Stages 2–7 | |

EXAMPLE 12

Using the same materials and formulations as those of Example 5, dry coatings were carried out employing a high speed agitation type mixing granulator Laboratory Matrix LMA-10 (500 g scale) over a period of 3 minutes, 5 minutes, 10 minutes, and 30 minutes. The physical properties of the prepared dry powder inhalations were measured which showed a good flowability with the angle of repose of 42°, indicating that it is possible to directly fill the capsule with the powder. The preparation had a loose apparent density (g/ml) of 0.62. A scanning electromicrograph (ABT-55 Topcon Corp.) of these preparations showed that the micronized active ingredient was uniformly adhered around the carrier particles if the coating times were 5 and 10 minutes, but somewhat non-uniform adherence was observed at a coating time of 3 minutes; and non-uniform adherence was observed with 30 minutes. Measurement of content uniformity with liquid chromatography for a coating time of 5 minutes showed it was uniform.

EXAMPLE 13

Using the same materials and formulation as those of Example 6, dry coating was carried out employing a high speed agitation type mixing granulator Vertical Granulator VG-01 Model (100 g scale) over a period of 5 minutes and 10 minutes. The physical properties of the prepared dry powder inhalation were measured which showed a good flowability with the angle of repose at 40.50, indicating that it is possible to directly fill the capsule with the powder. The preparation had a loose apparent density (g/ml) of 0.68. A scanning electromicrograph (ABT-55 Topcon Corp.) of these preparations showed that the micronized active ingredient was uniformly adhered around the carrier particles if the coating times were 5 and 10 minutes.

EXAMPLE 14

With the objective of investigating the dispersibility of the active ingredient (10% content) from the carrier particles in the dry powder inhalation prepared at a dry coating for 5 minutes in Example 12, the preparation was dispersed with the various spray pressure; and the state of dispersion was measured using a laser diffraction particle size analyzer (LDSA-1400AI: Tonichi Computer Applications Company) to measure the dispersion ratios of the active ingredient of 10 µm or less. It was verified that the carrier particles and active ingredient were re-dispersed even at very low dispersion pressures (Table 19).

TABLE 19

Results of Particle Size Distribution

| Spray Pressure | Dispersibility of Active Ingredient (%) |
|---|---|
| 0.2 kg/cm$^2$ | 8.6 |
| 0.3 kg/cm$^2$ | 9.8 |
| 0.5 kg/cm$^2$ | 10.6 |

EXAMPLE 15

The preparation from the 5 minute-dry coating obtained in Example 12 was filled into HPMC capsules (The Japanese Pharmacopeia No. 2 capsule: Shionogi Qualicaps Co., Ltd.), showing good filling capabilities and permitting a dry powder inhalation with 40.9 mg of the content filled therein to be prepared. The filling machine used was an LIQFIL Super40 (Shionogi Qualicaps Co., Ltd.) employing a die-compress type powder filling system (Table 20).

TABLE 20

Results of Filling Experiments

| Weight of Empty Capsule (mg) | 59.4 |
|---|---|
| Weight of Filled Capsule (mg) | 100.3 |
| Weight of Capsule Content (mg) | 40.9 |

EXAMPLE 16

An in vitro test was made using the capsule prepared in Example 15. The HPMC capsule filled with about 40 mg of the micronized preparation (The Japanese Pharmacopeia No. 2 capsule: manufactured by Shionogi Qualicaps Co., Ltd.) was mounted on an inhaler device (Jethaler®; Unisia Jecs Corp.). The Jethaler® brand device was then attached to the mouthpiece of a cascade impactor (Anderson sampler; Model AN-200) and inspired at a flow rate of 28.3 L/min., thereby dispersing the micronized preparation in the capsule and measuring the residual active ingredient in the capsule and in the inhaler device as well as the distribution of the active ingredient at each stage. The results are given in Table 21. It was shown that in the in vitro test with the cascade impactor, the lung delivery fraction at stages 2–7 corresponding to the respiring fraction was about 40%. The contents were removed from the filled capsule and the dispersibility of the active ingredient (10% content) coated on the carrier particle surface was measured, at various spray pressures, using a laser diffraction particle size analyzer (LDSA-1440A: Tonichi Computer Applications Company) to measure the re-dispersion ratio of the active ingredient of 10 µm or less. Good dispersibility at a low spray pressure (Table 22) similar to the results in Table 19 was shown, and no changes were observed in physical properties by the filling.

TABLE 21

Results of in vitro Test

| Results of in vitro Test | (Unit, %) |
|---|---|
| Capsule | 1.5 |
| Device | 14.6 |
| Throat | 16.9 |
| Stage 0 | 21.9 |
| Stage 1 | 2.4 |
| Stages 2–7 | 42.7 |

TABLE 22

Particle Size Distribution of Filled Preparations

| Spray Pressure | Dispersibility of Active Ingredient (%) |
|---|---|
| 0.2 kg/cm$^2$ | 7.5 |
| 0.3 kg/cm$^2$ | 8.8 |
| 0.5 kg/cm$^2$ | 9.6 |

EXAMPLE 17

Lactose micronized by a jet mill (mean particle diameter: 1.5 µm), 1%, and carrier trehalose particles (mean particle diameter: 81 µm) similarly to Example 4, 89%, were pre-mixed to which mixed powder was added S-36496, 10%, followed by dry coating for 5 minutes using a high speed agitation type mixing granulator, Vertical Granulator VG-01 (Powrex Company) (100 g scale). The dispersibility of the active ingredient (10% content) from the carrier trehalose particles using the prepared dry powder inhalation was measured by dispersing with the various spray pressure, whereby the state of dispersion was measured using a laser diffraction particle size analyzer (LDSA-1400A: Tonichi Computer Applications Company) to measure the dispersion ratios of the active ingredient of 10 µm or less. It was verified that as shown in Table 23, the carrier trehalose particles and active ingredient can be re-dispersed even at a very low dispersion pressure.

A capsulated preparation (The Japanese Pharmacopeia No. 2 HPMC capsules: manufactured by Shionogi Qualicaps Co., Ltd.) filled with about 40 mg of the prepared dry powder inhalation was prepared and mounted on an inhaler device (Jethaler; Unisia Jecs Corp.) The Jethaler was then attached to the mouthpiece of a cascade impactor (Andersen sampler; Model AN-200) and inspired at a flow rate of 28.3 L/min., thereby dispersing the dry powder inhalation in the capsule and measuring the residual active ingredient in the capsule and in the inhaler device as well as the distribution of the active ingredient at each stage with liquid chromatography. The results are given in Table 24. It was confirmed that in the in vitro test with cascade impactor, the dry powder inhalation prepared by the Vertical Granulator showed a stages 2–7 delivery fraction equivalent to that of the dry powder inhalation prepared by the Mecahnomill described in Example 9. This suggests that the present preparation method using trehalose is a procedure which can be scaled up.

TABLE 23

| Spray Pressure | Dispersibility of drugs (active ingredient) (%) |
|---|---|
| 0.2 kg/cm² | 8.3 |
| 0.3 kg/cm² | 9.4 |

TABLE 24

| | Residual and Distributed Fractions of Active Ingredient S-36496 (%) |
|---|---|
| Capsule | 7.3 |
| Inhaler device | 19.4 |
| Throat | 15.0 |
| Stage 0 | 22.3 |
| Stage 1 | 5.8 |
| Stages 2–7 | 30.2 |

EXAMPLE 18

The extent of improvement in taste was measured for the dry powder inhalation of this invention. A bitter tasting material was used, similar to Example 4, along with trehalose (mean particle diameter: 81 μm) or lactose (Lactose 325M, mean particle diameter: 66 μm manufactured by DMV Co.) as a carrier and with trehalose (mean particle diameter: 1.4 μm) as a surface modifier to prepare a dry powder inhalation according to the method of Example 6. An about 10 mg portion of the preparation was sampled on a spatula and was then directly placed on the tongue to compare the taste. The preparation formulated using Lactose 325M brand lactose as a carrier tasted bitter, but one formulated using trehalose as a carrier tasted sweet. Therefore, the dry powder inhalation formulated using trehalose as a carrier softened the bitterness of the active ingredient and clearly improved the taste, making it palatable for the pediatric and elderly patients.

EXAMPLE 19

The extent of improvement in taste was tested for the dry powder inhalation of this invention. A bitter tasting material was used, similarly to Example 4, along with trehalose (mean particle diameter: 81 μm) or Lactose 325M (mean particle diameter: 66 μm) as a carrier and with trehalose (mean particle diameter: 1.4 μm) as a surface modifier to prepare a dry powder inhalation according to the method of Example 6. An about 10 mg portion of the preparation was sampled on a spatula and was then directly placed on the tongue to compare the taste. The preparation formulated the Lactose 325M as a carrier tasted bitter, but one formulated trehalose as a carrier tasted sweet. Therefore, the dry powder inhalation formulated trehalose as a carrier softened the bitterness of the active ingredient, clearly improving the taste making it palatable for the pediatric and the elderly patients.

EXAMPLE 20

Micronized adhering lactose and carrier particles were premixed to which mixed powder was added Ethanbutol hydrochloride according to the formulations given in Table 25 below, followed by dry coating for 5 minutes and 10 minutes using a high speed agitation type mixing granulator, Vertical Granulator VG-01 (Powrex Co.) (50 g scale). The prepared dry powder inhalation was observed with a scanning electron microscope (ABT-55 Topcon Corp.), which confirmed the uniform dry coating of micronized active ingredient was made around the carrier particles in dry powder inhalation prepared by each coating time.

TABLE 25

| | Formulations | |
|---|---|---|
| Component | | Composition (%) |
| Ethanbutol Hydrochloride | | 5.0 |
| Micronized Lactose | | 1.5 |
| Erythritol | | 93.5 |

EXAMPLE 21

Micronized adhering trehalose, 1%, and carrier trehalose particles, 96%, were premixed to which mixed powder was added Butenafine hydrochloride, 3%, followed by dry coating for 5 minutes using a high speed agitation type mixing granulator, Vertical Granulator VG-01 (Powrex Co.,) (100 g scale). The prepared dry powder inhalation was observed with a scanning electron microscope (ABT-55 KK Topcon), which confirmed the uniform dry coating of micronized active ingredient was made around the carrier trehalose particles.

EXAMPLE 22

Micronized adhering lactose and carrier particles of erythritol were premixed to which mixed powder was added Mabuterol hydrochloride according to the formulations gvien in Table 26 below, followed by dry coating for 5 minutes using a Theter Composer (manufactured by Tokuju Kosakusho Co., Ltd.) (6 g scale). The prepared dry powder inhalation was observed with a scanning electron microscope (ABT-55 KK Topcon), which confirmed that the uniform dry coating of micronized active ingredient was made around the carrier particles.

TABLE 26

| Formulationws | |
|---|---|
| Component | Composition (%) |
| Mabuterol Hydrochloride | 1.0 |
| Micronized Lactose | 0.2 |
| Erythritol | 98.8 |

EXAMPLE 23

Micronized adhering trehalose, 1%, and carrier trehalose particles, 98.5%, were premixed to which mixed powder was added Mabuterol hydrochloride, 0.5%, followed by dry coating for 5 minutes using a high speed agitation type mixing granulator, Vertical Granulator VG-01 (Powerex Co.) (50 g scale). The prepared dry powder inhalation was observed with a scanning electron microscope (ABT-55KK Topcon), which confirmed the uniform dry coating of micronized active ingredient was made around the carrier trehalose particles. This indicates that a dry powder inhalation using the carrier trehalose can also be used for many pharmaceutically active ingredients.

INDUSTRIAL UTILITY

As described above, the dry powder inhalation of this invention shows good inhalation behavior of the active ingredient. In addition, it improves the taste in inhalation and reduces the discomfort in the oral cavity and the throat. It can be readily prepared without any complicated processes, with minimal risks of adhesion-agglomeration, caking, and deliquescence during the preparation or storage, making it possible for the dry powder inhalation to be filled into a capsule for an application in capsulated form or a preparation for use in an inhaler device.

What is claimed is:

1. A dry powder inhalation selected from the group consisting of:

(a) a dry powder inhalation containing a micronized pharmaceutically active ingredient, a micronized surface modifier, and a carrier particle, wherein at least the micronized pharmaceutically active ingredient and the micronized surface modifier are adhered to the surface of the carrier particle, and the carrier particle is at least one of erythritol or trehalose, and the micronized pharmaceutically active agent is S-36496;

(b) a dry powder inhalation having at least a micronized pharmaceutically active ingredient comprising S-36496 and a micronized surface modifier comprising lactose and having a mean particle diameter of not more than 3 μm adhered to the surface of a carrier particle comprising erythritol and having a mean particle diameter of from 50 to 90 μm.

2. A dry powder inhalation according to claim 1, wherein said dry powder inhalation is (b).

3. A dry powder inhalation as according to claim 2, wherein wherein said dry powder inhalation said carrier particles have a mean particle diameter of about 80 μm.

4. A dry powder inhalation according to claim 2, wherein said dry powder inhalation said micronized surface modifier has a mean particle diameter of 1. 5 μm.

5. A dry powder inhalation according to claim 2, wherein said dry powder inhalation has an angle of repose of not more than 45°.

6. A dry powder inhalation according to claim 2, wherein the micronized active ingredient has a particle size in terms of a mean particle diameter of 1 to 6 μm.

7. A dry powder inhalation according to claim 1, wherein in the micronized surface modifier has a particle size in terms of a mean particle diameter of not more than 3 μm.

8. A dry powder inhalation according to claim 2, wherein the content of the carrier particles is 79.9–99 mass % of the total weight of dry powder inhalation.

9. A dry powder inhalation according to claim 2, wherein the content of the micronized active ingredient is 0.01–20 mass % of the total dry powder inhalation.

10. A dry powder inhalation according to claim 2, wherein the content of the micronized surface modifier is 0.1 to 2% of the total weight of dry powder inhalation.

11. A dry powder inhalation according to claim 2, wherein the dry powder inhalation is in a capsule dosage form.

12. A method for preparing the dry powder inhalation according to claim 4, wherein said method comprises mixing the micronized active ingredient and carrier particles, with the addition of a micronized surface modifier; and then dry coating.

13. A method for preparing the dry powder inhalation according to claim 12, wherein the micronized active ingredient is prepared by a dry pulverizer.

14. A method for preparing the dry powder inhalation according to claim 12, wherein the micronized surface modifier is prepared using a dry pulverizer.

15. A method for preparing the dry powder inhalation according to claim 12, wherein at least one of the micronized active ingredient or the micronized surface modifier is prepared using a jet mill.

16. A method for preparing the dry powder inhalation according to claim 12, wherein at least one of the micronized active ingredient or the micronized surface modifier is prepared using a pulverizer and wherein, the entire processes of pulverization, mixing, and coating are carried out in dry method without a solvent.

17. A dry powder inhalation as set forth in claim 1, wherein said dry powder inhalation is in a capsule dosage form, said dry powder inhalation is (a), said micronized surface modifier having a particle size in terms of a mean particle diameter of 0.1 to 3 μm, said micronized surface modifier is lactose, said carrier particles having a particle size in terms of a mean particle diameter of 50–90 μm, said micronized pharmaceutically active ingredient having a particle size in terms of a mean particle diameter of 1 to 3 μm, the content of the micronized surface modifier is 0.1 to 2% of the total weight of the dry powder inhalation, and the content of the micronized pharmaceutically active ingredient is 0.01–20 mass % of the total dry powder inhalation.

18. A dry powder inhalation as according to claim 1, wherein in (a) the carrier particle is erythritol and the micronized surface modifier is lactose and/or trehalose.

19. A dry powder inhalation according to claim 1, wherein in (a) the carrier particle is trehalose and the micronized surface modifier is lactose and/or trehalose.

* * * * *